United States Patent [19]

Njieha et al.

[11] Patent Number: 5,070,188

[45] Date of Patent: Dec. 3, 1991

[54] ACYLATED EPIDERMAL GROWTH FACTOR

[75] Inventors: Francois K. Njieha, New Brunswick; Shalaby W. Shalaby, Lebanon, both of N.J.

[73] Assignee: Ethicon, Inc., Somerville, N.J.

[21] Appl. No.: 383,518

[22] Filed: Jul. 24, 1989

[51] Int. Cl.$^5$ ............................................... C07K 7/10
[52] U.S. Cl. ...................................... 530/324; 530/399
[58] Field of Search ................... 530/324, 399; 514/12, 514/2

[56] References Cited

U.S. PATENT DOCUMENTS 4,731,357 3/1988 Franklin et al. .................. 514/12 X
4,743,679 5/1988 Cohen et al. .................... 530/324 X Primary Examiner—Howard E. Schain
Attorney, Agent, or Firm—Richard J. Grochala

[57] ABSTRACT

The present invention provides acylated epidermal growth factor derivatives, methods of making the derivatives and pharmaceutical compositions containing the derivatives.

4 Claims, No Drawings

ACYLATED EPIDERMAL GROWTH FACTOR

BACKGROUND OF THE INVENTION

The present invention concerns chemically modified forms of epidermal growth factor (EGF) in which the EGF is modified by acylation. The invention also relates to pharmaceutical compositions containing acylated EGF which have increased biological stability and resistance to proteolytic degradation.

Human EGF (also known as urogastrone) is a 53 amino acid polypeptide growth factor that has mitogenic activity for different types of cells, including epithelial and mesenchymal cells. Variants of the human EGF polypeptide have been reported, such as the 52 amino acid gamma-urogastrone. EGF has been reported to be useful in increasing the rate of wound healing as a result of its mitogenic activity. EGF has also been reported as being useful for treating gastric ulcers, cerebral ischemia and psoriasis. A review of EGF is provided by Carpenter et al., in "Epidermal Growth Factor, Its Receptor and Related Proteins," Experimental Cell Research, 164: 1-10 (1986).

The topical or oral therapeutic administration of proteins and peptides is generally hampered because of rapid proteolytic degradation and low absorption from the application sites. EGF is currently used topically to treat wounds, including burns, donor site wounds, and ulcers. EGF also has applications in the treatment of disease conditions such as gastric ulcers and ischemia and reperfusion injuries. The delivery of EGF to patients either parenterally with implanted devices, topically or orally has not been as successful as anticipated. It is believed that this may be a result of loss of biological activity or enzymatic degradation of the EGF molecule. To date, efforts to develop dosage forms for mucosal (e.g., nasal or buccal) or oral delivery have been discouraged specifically because of either low absorption and/or the anticipated inactivation by proteolytic enzymes. Also, for indications in which aqueous solutions of EGF were the preferred dosage form, the practical shelf life of such formulations was questionable.

A limited number of reports on the efficacy of EGF for treating peptic ulcer formation and the healing of chronic gastric ulcers support the protective and curative effects of EGF in these applications. However, the full pharmacological potential of EGF in these applications could not be achieved even when the drug was administered intravenously. Limited success has been reported when EGF is administered in exceptionally large oral doses. As mentioned above, this could be explained in part because of the results of proteolytic degradation and/or low absorption of EGF from the respective dosage forms and/or poorly targeting dosage forms for the duodenal mucosa.

It is also believed that EGF in topical dosage forms are prone to proteolytic degradation by wound proteinases or proteinases from contaminating wound microflora. For wound healing applications, topical dosage forms containing a less proteolytically susceptible EGF will have a prolonged therapeutic efficacy.

SUMMARY OF THE INVENTION

The present invention provides a chemically modified form of EGF which overcomes the disadvantages of the unmodified, native EGF used prior to the present invention. The modified EGF of the present invention is acylated at one or more of the primary amino acids on residues asparagine 1, lysine 28 or lysine 48. Preferably the EGF is human EGF and is used in a pharmaceutical composition for treating wounds, gastric ulcers, cerebral ischemia or psoriasis. It has been found that EGF can be modified by acylation without any detectable loss in its biological activity, namely mitogenic activities for epithelial and mesenchymal cells and the inhibition of gastric acid secretion. In accordance with the present invention, EGF may be acylated with acyl groups having the general formula:

wherein R is an aliphatic or aromatic residue.

DETAILED DESCRIPTION OF THE INVENTION

Human EGF refers to the EGF having that polypeptide sequence, or any substantial portion thereof, as set forth in Urdea, M. S. et al., Proc. Natl. Acad. Sci. USA, 80: 6461-6465 (1983). Native human EGF refers to EGF having the 53 amino acid sequence set forth in Undea et al. Human EGF also refers to any human EGF variants, such as gamma-urogastrone. The EGF useful in the present invention may be isolated from natural sources, produced using recombinant DNA techniques or prepared by chemical synthesis. EGF obtained from any of these sources may then be acylated according to the methods described herein and then used in wound healing or gastric ulcer healing applications.

As used herein "acylation" refers to the introduction of one or more acyl groups into the EGF molecule. The acyl groups covalently bond to one or more of the primary amino acids on residues at the N-terminus (e.g., asparagine 1), lysine 28 and lysine 48. An acyl group is any organic acid group in which the hydroxyl group of a carboxyl group is replaced by some other substituent. Thus, an acyl group has the general formula

wherein R is an aliphatic or aromatic residue. Common examples of acyl groups include $CH_3CO-$ (an acetyl group) and $C_6H_5CO-$ (a benzoyl group). Examples of aliphatic (straight chain and cyclic) and aromatic residues which may be substituted for R in the acyl groups useful in the present invention are $CH_3-$; $C_nH_{2n+1}$ (where n=2 to 20); cyclic $C_nH_{2n-1}$ (where n=3 to 6); substituted or unsubstituted phenyl, pyridyl or naphthyl; $R^1-CH_2$, where $R^1$ is $CH_3O-$ a low to high molecular weight alkylene oxide chain; haloalkyl; or a mono- or polysaccharide.

EGF may also be acylated with bifunctional acylating agents having the general formula $HOOC-(CH_2)_n-COOH$, wherein n=0-14. The resulting acylated EGF would then consist of two EGF molecules bridged together and having the formula:

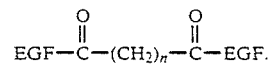

The present methods may be used to selectively acylate EGF at any of its reactive primary amines to produce a variety of monoacylated, diacylated or triacylated versions of EGF. In each case, the acyl group is covalently bonded to one or more of the primary amines on amino acid residues asparagine 1 (or whatever the N-terminal amino acid might be), lysine 28 and lysine 48. Selective acylation may be achieved by the use of protective blocking groups to block those reactive primary amines which are not to be acylated. The use of such blocking groups is well known in the art as set forth, for example, in J. F. W. McOmie, *Protective Groups and Organic Chemistry*, Plenum Press, New York, 1973. EGF monoacylated at the N-terminus may be represented by the formula:

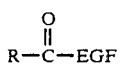

in which the acyl group covalently bonds to the primary amino group of the N-terminal amino acid. Monoacylated and diacylated versions of EGF in which the acyl group is bound to the epsilon primary amino group of lysine 28 and/or lysine 48 may be represented by the formulas:

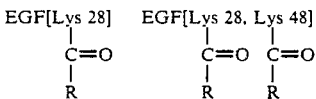

Of course, the acyl group may be present in any combination at the three reactive primary amines mentioned above to form a variety of mono-, di- and triacylated EGF molecules. In a preferred embodiment of the present invention, the EGF is triacylated with the same acyl group.

The acylated EGF of the present invention is superior to unmodified, native EGF in that the acylated EGF unexpectedly retains its biological activity under physiological conditions. Acylated EGF is resistant to proteolytic degradation. Therefore, it may be useful in parenteral formulations as well as topical formulations. It is believed that the acylated EGF, when used in a pharmaceutical composition, is more lipophilic and provides a longer acting and controlled release form of EGF. Acylation may be conducted by any of the standard methods employed in peptide chemistry, including the use of activated esters, acid halides, acylated heterocyclic nitrogen compounds or anhydrides. Examples of acylating agents useful to make the EGF of the present invention include acetic, succinic, maleic or methylmaleic anhydrides; esters of N-hydroxysuccinimide, N-acylimidazoles and N-acylpyrrazoles. General methods of acylation are set forth in *Methods In Enzymology*. 25: 494–499 (1972), which is incorporated herein by reference.

The acylating reactions used to prepare acylated EGF are suitably carried out in aqueous buffered media (including those with DMSO containing limited concentrations of aqueous buffer solution) at a pH range which is not detrimental to the EGF, acylating agent or acylated EGF, e.g., from pH 6.5 to pH 9.5 and preferably at approximately pH 7.5. The reaction is generally carried out by mixing the acylating agent with EGF at a moderate temperature, which is in the range of 20° to 40° C. The concentration of acylating agent used is adjusted according to the reactivity of the agent, its solubility and the level of acylation desired. The time for which the reaction is allowed to proceed depends upon the acylating agent used and the temperature at which the reaction is carried out. A convenient time is about 1 hour to about 12 hours at about 30° C., but the reaction may be allowed to continue for a longer period of time.

After the acylating reaction is complete, the acylated EGF derivative is purified by standard methods such as dialysis, affinity chromatography, and ultrafiltration, and thereafter recovered by standard methods such as freeze-drying from aqueous media. Where necessary, the acylated EGF may be adapted, for example, by sterilization, for intravenous administration to human beings.

Acylation of EGF results in a modified form of EGF which has a higher charge density than native EGF and which may be useful for controlled delivery by iontophoresis. By blocking the amine groups with acyl groups, the net charge of the EGF is increased and its isoelectric point is lowered. This in turn increases the mobility of the acylated-EGF in transport processes which are driven by electrical charge, such as iontophoresis.

It is contemplated that the other growth factors, such as fibroblast growth factors, platelet-derived growth factors and insulin or insulin-like growth factors may be modified according to the teachings of the present invention. It is also contemplated that the stabilization of EGF, growth factors and other proteins may be achieved, similarly, by phosphorylation and esterification of reactive amino acid residues. Since arginine residues represent a site for proteolytic cleavage, such as by tryptic cleavage, blocking of the arginine guanidinium group via cycloalkylation (by using a vinyl ketone) may impart stability to such molecules.

The acylated EGF derivatives of the present invention are preferably administered to humans as pharmaceutical compositions. Accordingly, the present invention also provides a pharmaceutical composition comprising an acylated EGF derivative in a pharmaceutically effective amount in combination with a pharmaceutically acceptable carrier. Such compositions are formulated in accordance with routine procedures used to prepare pharmaceutical compositions for administration to humans. Typically, compositions for intravenous administration are solutions of sterile acylated EGF and sterile isotonic aqueous buffer. Where necessary, the composition may also include a solublizing agent to keep the derivative in solution.

A "pharmaceutically effective amount" of acylated EGF refers to that amount which provides a therapeutic effect in various administration regimens. For example, when used for wound healing purposes, it is that amount which is necessary to enhance the rate of healing the wound. The compositions of the present inventions may be prepared containing amounts of acylated EGF within the range of from about 0.01 to about 1000 micrograms per milliliter of an aqueous or non-aqueous formulation. Preferably, the concentration is in the range 1–500 micrograms per milliliter and more preferably in the range 1–100 micrograms per milliliter.

As EGF has been described as being useful in wound healing and treating gastric ulcers, the compositions of the present invention containing acylated EGF may be used to treat wounds and gastric ulcers so as to increase the rate of healing thereof. The types of wounds that may be healed using the compositions of the present invention are those which result from accidental or medical injury which cause epithelial damage, such as ophthalmic wounds, such as those which result from corneal abrasions, corneal ulcers, radial keratotomy, corneal transplants, epikeratophakia and other surgically-induced wounds in the eyes; and cutaneous wounds such as burn wounds, donor site wounds from skin transplants and ulcers (cutaneous, decubitis, venous stasis and diabetic). Additionally, dermatological conditions in which the skin has been damaged such as psoriasis, sunburn and skin rashes, may be treated with the compositions of the present invention. The compositions may be applied to the wound site either topically or internally depending on the type of wound. In addition to the above-mentioned wound healing applications, the compositions of the present invention may be useful in cancer therapy, gastrointestinal protection during gastric ulcer treatment and gastric ulcer treatment.

Methods for increasing the rate of healing the wound comprise applying or contacting the compositions of the present invention directly to the wound by topically administering the composition to a wound site. The composition is permitted to remain in contact with the wound for a period of time sufficient to increase the rate of cell growth at the wound site. Such methods include incorporating any composition of the present invention into any pharmaceutically acceptable controlled release composition, such as a cream, gel, aerosol spray, microcapsules, films or lyophilized foams or aqueous formulation or soaking a gauze dressing with an aqueous solution of the composition and then applying such formulations or dressings to the wound site.

The compositions of the present invention are useful in eyedrop formulations, eye gels, eye creams, liposome or micell formulations, aqueous vehicles for soaking gauze dressings, burn dressings, artificial skins, sutures and staple coatings, salves or creams (aqueous or non-aqueous), gel formulations, foams and the like. Additional materials, such as buffers, preservatives, tonicity adjusting agents, anti-oxidants, polymers for adjusting viscosity or for use as extenders, and excipients may be used in the compositions. Specific illustrative examples of such other material include acetate or borate buffers; thimerosol, sorbic acid, methyl or propyl paraben and chlorobutanol preservatives; sodium chloride and/or sugars to adjust the tonicity; and excipients such as mannitol, lactose or sucrose.

The following examples are presented to illustrate the subject invention. The invention is not to be considered limited by these examples, but only by the appended claims.

EXAMPLE I

Preparation of Acylated EGF

A variety of acylated EGF molecules were prepared according to the following method using acyl groups ranging from acetyl ($C_2$) to stearoyl ($C_{18}$). Recombinantly produced human EGF (obtained from Chiron Corporation, Emeryville, Calif.) was lyophilized with mannitol as an extender. The lyophilized EGF was then used to prepare acylated EGF. The lyophilized EGF is dissolved in a buffered aqueous or non-aqueous media at concentrations of 0.5 to 2 mg/ml. Preferentially, the media is selected according to the solubility of the modifying reagents cited above and is buffered with polyionic reagents selected according to their solubility in the media. For long chain acyl groups, the preferential media is DMSO buffered with triethanolamine or ammonium acetate to a final pH of 7.5–8.5. Ammonium acetate is also generally used for aqueous buffer systems of reactions, although Tris-base HEPES, TES, and phosphate buffers may also be used.

Typically, 5 mg of EGF in 600 mg of mannitol is dissolved in 10 ml of DMSO containing 100 microliters of ethanolamine. While stirring, a total of 300 microliters of acetic anhydride is added slowly in three different aliquots during a period of two to three hours at 30° C. The pH of the solution is continuously adjusted to 7.5 with excess triethanolamine. After 1.5 hours incubation under the same conditions, aliquots are removed and assayed for the primary amine content. For this purpose, aliquots are diluted to 5 to 15 micrograms/ml and reacted with methoxy diphenyl furanone (Poly Science) in sodium borate buffer. The content of the fluorescence of the treated sample is compared with that of the control sample incubated without the acylating reagents. Modification is assumed completed when less than 10%, preferably 5%, of the original fluorescence intensity is observed in a typical reaction mixture. Otherwise, the incubation time is lengthened and/or excess modifying reagent added. Alternatively, the extent of reaction is determined by High Performance Liquid Chromatography (HPLC) of the diluted aliquots on a cation exchange column. The retention times of the modified species are compared with that of unmodified EGF. Under these conditions, the extent of modification is calculated from the chromatogram of the samples. Reaction is validated as described above.

The volume of the reaction mixture is adjusted to 30 ml with cold distilled deionized, pyrogen-free water. The diluted mixture is transferred to an appropriate dialyzing tubing (Spectrum) and dialyzed against three changes of two liters each of 0.5M $NH_4HCO_3$ buffer, pH 7.5 and one change of 50 mM $NH_4HCO_3$ buffer for 8–12 hours per change. Dialysis is carried out at 4°–20° C., preferably at 4° C. Dialyzed samples are concentrated by lyophilization and reconstitution in a small amount of 0.5M $NH_4HCO_3$ buffer at a concentration of 0.1 to 0.5 mg/ml. Final chromatography is run on an Ex-Cellulose (Pierce) desalting column. Preferably, the mixture is fractionated on a preparative cation exchange column. Eluents are collected on a Frac-200 (Pharmacia) fraction collector. Peak fractions representing molecules with different degrees of modification are pooled and desalted by dialysis. After sterilization by filtration, aliquots are dispensed or lyophilized in the presence of mannitol.

Protein concentration is determined by UV spectrophotometry at 278 nm using the extinction coefficient of 23.6 for a 1% solution or a standard curve using unmodified EGF as the standard. Similarly, EGF and the modified derivatives are determined by fluorescence spectrophotometry with excitation/emission at 225/350 or at 280/350 nm.

Samples are further analyzed by testing the biological activity in the Receptor Binding Assay (RBA) system and/or in a mitogenic assay system according to the standard procedure. Under these conditions, the extent of activity of modified EGF was compared with that of the unmodified EGF on a weight per weight basis. A similar test is used to follow the stability of EGF products. The RBA is described in Savage et al., Analytical Biochem, 111, pages 195 et seq. (1981) and in U.S. Pat.

No. 4,717,717. For RBA studies, a cell line with a high density of receptors for EGF is grown to confluency in microwell plates. After removing the growth media and slightly fixing the cells, the binding of modified EGF to the cell surface in the presence of competing iodinated-EGF is compared with the binding of non-radioactive, unmodified EGF under the same conditions. The concentration of modified EGF is extrapolated from the standard curve made for unmodified EGF. Acylated EGF with acyl side chains ranging from $C_2$ to $C_8$ retained biological activity according to the RBA.

For mitogenic assay systems, an EGF sensitive cell line is grown to confluency at the bottom of microwell plates. After replacing the regular growth media with growth factor poor media, modified EGF is added with tritium labelled thymidine. The extent of incorporation of the tritium labelled thymidine in the presence and absence of growth factors is then weighed. The effects of modified EGF are compared with those of unmodified EGF under the same system. In the mitogenic assay, acylated EGF having an acyl side chain of $C_{12}$ was nearly as reactive as $C_2$.

EXAMPLE II

In Vitro Susceptibility of Acylated EGF to Proteolytic Degradation

This example concerns the stability of acylated EGF ($C_2$-EGF) toward trypsin. The $C_2$-EGF was triacylated with acetyl groups. The results indicate that over 75% of the $C_2$-EGF resisted proteolytic cleavage at two of the susceptible bonds, namely Arg 41 and Arg 45, for over 4 hours incubation at 30° C. Under similar conditions, native EGF underwent over 65% cleavage within 5 minutes post-incubation period. The remaining 35% of the native molecules were cleaved within 2 hours post-incubation period. The resistance of $C_2$-EGF may be associated with the acylation of the lysine residues, and in particular, lysine-48 because trypsin cleaves peptide linkages at the carbonyl end of arginine or lysine residues. In native EGF, arginine 48 was cleaved faster by trypsin. Tryptic digestion of native EGF, acylated EGF ($C_2$-EGF) and the mixture of $C_2$-EGF and native EGF were analyzed by HPLC (Waters-845) on a polysulfoethyl aspartamide (Nest Group) cation exchanger column. The results indicate that tryptic fragments of native EGF could be readily separated from the native molecules. Under similar conditions, trypsin did not generate any fragment from the $C_2$-EGF which generally eluted faster than the native EGF or two of the major fragments from the N-terminal end of native EGF. The mixture of $C_2$-EGF and native EGF at a ratio of 1.5 to 1 was incubated with TPCK-trypsin (Worthington Biochem Corp.). At time intervals, aliquots were removed and analyzed. The results indicated a rapid decrease in the native EGF peaks with an increase in peaks for the native EGF fragments. Within about 20 minutes, over 85% of the native EGF was digested. In contrast, $C_2$-EGF lost only about 20% of its initial amount within 2.5 minutes post incubation. The remaining 75-80% resisted proteolysis up to 4 hours incubation.

These results show that simple acylation of the primary amine groups in EGF protects the molecules against degradation by trypsin, an example of an upper gastrointestinal tract endopeptidase. Based on these results it is believed that acylation imparts stability to EGF and hence, allows its prolonged activity for use in treatment of not only digestive ulcers, but also in topical wound healing applications.

EXAMPLE III

Shelf Stability of Acylated EGF

The shelf stability of EGF and acylated EGF derivatives with different degrees of modification and acyl side chains was studied using the Receptor Binding Assay (RBA) system. The results indicated that acylated EGF retained over 30% more activity when stored at 37° C. than the control unmodified native EGF. Table I below sets forth the results.

TABLE I

| | | Stored Time/Temperature | |
|---|---|---|---|
| Materials | 0 (%) | 2 months/4° C. (%) | 2 months/37° C. (%) |
| Control EGF | 100 | 81.09 | 57.52 |
| $C_2$-EGF | 100 | 88.67 | 87.37 |
| $C_6$-EGF | 100 | 61.88 | 66.94 |
| $C_8$-EGF | 100 | 83.19 | 69.04 |

Control EGF retained 81% of the original activity when stored at 4° C. and only 58% at 37° C. during the 2 month storage period. Acylated EGF ($C_2$-EGF) retained 81% of its activity at 4° C. and 88% at 37° C. during the same period. This provides an improvement of 30% over control on the basis of the 37° C. data. The higher stability of acylated EGF compared to control correlates with the high extent of modification and resistance to proteolytic degradation as reported above.

The invention has been described herein with reference to certain preferred embodiments and examples. Since obvious variations will appear to those skilled in the art, the invention is not to be considered limited thereto but only by the claims which follow.

What is claimed is:

1. A method for stabilizing epidermal growth factor (EGF) against proteolytic degradation, comprising:
   acylating the EGF at one or more of the primary amines of amino acid residues asparagine 1, lysine 28 or lysine 48.

2. The method of claim 1, wherein the EGF is acylated with acyl groups having the formula:

wherein R is an aliphatic or aromatic residue.

3. The method of claim 2, wherein the aliphatic residue is $C_1$-$C_{20}$ alkyl.

4. The method of claim 3, wherein the aliphatic residue is $C_1$-$C_6$ alkyl.

* * * * *